(12) United States Patent
Kemper et al.

(10) Patent No.: US 12,002,560 B2
(45) Date of Patent: Jun. 4, 2024

(54) SYSTEM AND METHOD FOR TESTING BLOOD VESSEL ACCESS USING POWERED FLUID INJECTOR SYSTEMS

(71) Applicant: BAYER HEALTHCARE LLC, Whippany, NJ (US)

(72) Inventors: Corey Kemper, Pittsburgh, PA (US); John Volkar, Valencia, PA (US); Michael Brooks, Croydon Park (AU); Leona Mulcahy, Epping (AU)

(73) Assignee: BAYER HEALTHCARE LLC, Whippany, NJ (US)

( * ) Notice: Subject to any disclaimer, the term of this patent is extended or adjusted under 35 U.S.C. 154(b) by 914 days.

(21) Appl. No.: 17/043,883

(22) PCT Filed: Apr. 8, 2019

(86) PCT No.: PCT/US2019/026256
§ 371 (c)(1),
(2) Date: Sep. 30, 2020

(87) PCT Pub. No.: WO2019/199632
PCT Pub. Date: Oct. 17, 2019

(65) Prior Publication Data
US 2021/0125697 A1 Apr. 29, 2021

Related U.S. Application Data

(60) Provisional application No. 62/655,365, filed on Apr. 10, 2018.

(51) Int. Cl.
*A61M 5/168* (2006.01)
*G16H 20/17* (2018.01)
*G16H 40/63* (2018.01)

(52) U.S. Cl.
CPC ........ *G16H 20/17* (2018.01); *A61M 5/16827* (2013.01); *G16H 40/63* (2018.01); *A61M 2205/3334* (2013.01)

(58) Field of Classification Search
CPC ...... A61M 2205/3334; A61M 5/16827; G16H 20/17
See application file for complete search history.

(56) References Cited

U.S. PATENT DOCUMENTS

| 7,925,330 B2 | 4/2011 | Kalafut et al. |
| 7,937,134 B2 | 5/2011 | Uber et al. |

(Continued)

FOREIGN PATENT DOCUMENTS

| JP | 4417621 B2 | 2/2010 |
| JP | 5203971 B2 | 6/2013 |

(Continued)

OTHER PUBLICATIONS

Bayer., "MRXperion OpManual—3038591 Rev H Feb. 13, 2018", Feb. 13, 2018.

(Continued)

*Primary Examiner* — Deanna K Hall
(74) *Attorney, Agent, or Firm* — James R. Stevenson; Bojan Popovic

(57) ABSTRACT

A fluid injector system has a controller for operably controlling the injection of contrast and/or saline into a patient. The controller allows a user to program a diagnostic injection procedure having one or more phases according to which the contrast and/or saline will be injected into the patient so as to effect enhancement of a region thereof during an imaging procedure. It further allows the user to program a test injection procedure to be performed prior to the diagnostic injection procedure. The test injection procedure is implementable as: (a) a variable single phase test injection (Continued)

in which the rate at which the saline is to be delivered is selectable prior to and may be varied during performance thereof; and/or (b) a multi-phase test injection in which the rate at which the saline is to be delivered is selectable for each phase of the multi-phase test injection prior to performance thereof.

25 Claims, 9 Drawing Sheets

(56) References Cited

U.S. PATENT DOCUMENTS

| | | | |
|---|---|---|---|
| 8,133,203 B2 | 3/2012 | Hack | |
| 8,160,679 B2 | 4/2012 | Uber et al. | |
| 8,295,914 B2 | 10/2012 | Kalafut et al. | |
| 8,915,399 B1 | 12/2014 | Nystrom | |
| 9,008,759 B2 | 4/2015 | Kalafut et al. | |
| 9,056,200 B2 | 6/2015 | Uber, III et al. | |
| 9,302,044 B2 | 4/2016 | Kalafut et al. | |
| 9,421,330 B2 | 8/2016 | Kalafut et al. | |
| 9,474,857 B2 | 10/2016 | Riley et al. | |
| 9,750,953 B2 | 9/2017 | Kalafut | |
| 9,913,941 B2 | 3/2018 | Miller et al. | |
| 9,949,704 B2 | 4/2018 | Kalafut et al. | |
| 9,959,389 B2 | 5/2018 | Kalafut | |
| 2007/0100282 A1* | 5/2007 | Small | A61M 5/14566 700/282 |
| 2010/0030073 A1 | 2/2010 | Kalafut et al. | |
| 2017/0258982 A1 | 9/2017 | Kemper | |

FOREIGN PATENT DOCUMENTS

| | | |
|---|---|---|
| WO | 2006044409 A2 | 4/2006 |
| WO | 2008085421 A2 | 7/2008 |
| WO | 2009149367 A1 | 12/2009 |
| WO | 2015106107 A1 | 7/2015 |
| WO | 2016112163 A1 | 7/2016 |

OTHER PUBLICATIONS

Bracco., "Put your CT Throughput in the Fast Lane, Introducing CT Express Brochure", 2016.
"International Preliminary Report on Patentability of PCT Application No. PCT/US2019/026256", dated Oct. 22, 2020.
Ulrich; Medical., "ulrichINJECT CT motion, CT contrast media injector from ulrich medical", Feb. 2016.

* cited by examiner

SYSTEM AND METHOD FOR TESTING BLOOD VESSEL ACCESS USING POWERED FLUID INJECTOR SYSTEMS

CROSS-REFERENCE TO RELATED APPLICATION

This application is a U.S. national phase application under 35 U.S.C. § 371 of PCT International Application No. PCT/US2019/026256, filed Apr. 8, 2019 and claims the benefit of U.S. Provisional Patent Application No. 62/655,365, filed Apr. 10, 2018, the disclosures of which are hereby incorporated by reference in their entirety.

BACKGROUND OF THE DISCLOSURE

Field of the Disclosure

The present disclosure is related to systems, methods, and computer program products for testing blood vessel access using a powered fluid injector and, more particularly, to systems and methods for testing acceptability of blood vessel access using a powered fluid injector configured for allowing an adjustment of fluid delivery rate during a test injection procedure. The present disclosure is further related to systems and methods for testing acceptability of blood vessel access using a powered fluid injector configured for having a plurality of injection phases during a test injection procedure.

Description of the Related Art

In many medical diagnostic and therapeutic procedures, a medical practitioner, such as a physician, injects a patient with one or more medical fluids. In recent years, a number of medical fluid delivery systems for pressurized injection of fluids, such as a contrast solution (often referred to simply as "contrast" or a "contrast medium"), a flushing agent, such as saline, and other medical fluids, have been developed for use in procedures such as angiography, computed tomography (CT), ultrasound, magnetic resonance imaging (MM), positron emission tomography (PET), and other imaging procedures. In general, these medical fluid delivery systems, such as powered fluid injectors, are designed to deliver such fluids via one or more injection protocols each comprising one or more phases to enhance regions of interest in a patient's body during a diagnostic imaging procedure. Examples of powered fluid injectors that are capable of delivering such fluids via user-programmable single phase or multi-phase diagnostic injection procedures include the MEDRAD® Stellant CT Injection System and the MEDRAD® MRXperion MR Injection System, both of which offered by Bayer HealthCare LLC.

In some injection procedures, fluid is delivered to a patient through a fluid path set or tubing having a proximal end thereof connected to the powered fluid injector and a distal end thereof connected to a vascular access device that is inserted into a blood vessel, such as a vein, of the patient. Special efforts are often made to assure a proper placement of the needle, the cannula, the catheter, the central line, or other vascular access device, as the case may be, in the patient's vessel to assure that the end thereof is clear (i.e., not clotted or otherwise obstructed), and fully inserted into the vessel without perforating the wall thereof. In some cases, extravasation may occur when fluid, such as contrast and/or saline, is injected into the surrounding tissue instead of the patient's vessel. In order to avoid extravasation of contrast and/or saline into the patient's tissue and to assure that the end of the vascular access device is not blocked and is in fluid communication with the vessel, a patency check may be performed.

The patency check provides confirmation that the fluid path set and the associated vascular access device is fluidly connected to the patient's blood vessel. A test injection may be performed with the powered fluid injector using a fixed volume of fluid, such as saline, at a fixed delivery rate. The volume and the rate of delivery of the fluid are fixed because prior art powered fluid injectors, such as the MEDRAD® Stellant and MEDRAD® MRXperion MR Injection Systems, are not currently capable of performing test injections in which the volume or flow rate can be varied, or where test injections can have more one than one phase. Such a test injection allows the clinician to check the suitability of the vessel access point to receive fluid at the same flow rate that will be used for the diagnostic injection. The clinician may visually observe and/or palpate the area near the injection site to assure that the vascular access device has been properly inserted into the vessel, while checking the tubing used therewith for any leaks. In some examples or aspects, the clinician may observe a pressure graph on the powered injector system to determine if an expected pressure is developed during the test injection. After the patency check is complete, a diagnostic injection procedure may be carried out by programming or otherwise selecting the desired diagnostic injection protocol.

While conventional patency check devices and methods are known in the medical field, improved patency check devices and methods continue to be in demand. Accordingly, it would be desirable to provide improved systems and methods for testing blood vessel access using a powered fluid injector.

SUMMARY OF DISCLOSURE

The present disclosure relates to systems, computer program products, and methods for testing acceptability of blood vessel access using a powered fluid injector system configured for allowing an adjustment of the rate at which fluid can be delivered during a test injection. The present disclosure further relates to systems, computer program products, and methods for testing acceptability of blood vessel access using a powered fluid injector system configured for performing test injections comprising a plurality of phases. Various examples or aspects of the present disclosure may be characterized by one or more of the following numbered clauses:

Clause 1. A fluid injector system comprising: a controller operably associated with at least one drive member by which at least one fluid contained within at least one fluid container is injectable into a patient, the controller including a programming system for enabling programming of at least one diagnostic injection procedure comprising at least one diagnostic injection phase according to which the at least one fluid is to be injected into the patient so as to effect enhancement of at least one region of interest thereof over a scan duration of a diagnostic imaging procedure; and the programming system for further enabling programming of a test injection procedure to be performed prior to the diagnostic injection procedure, wherein the test injection procedure is implementable as at least one of: (a) a variable single phase test injection in which a flow rate at which the at least one fluid is to be delivered is selectable prior to performance of the variable single phase test injection and may be varied during performance of the variable single phase test injection; and (b) a multi-phase test injection in which the flow rate at which the at least one fluid is to be delivered is selectable for each phase of the multi-phase test injection prior to performance of the multi-phase test injection.

Clause 2. The fluid injector system according to clause 1, wherein the test injection procedure is further implementable as a fixed single phase test injection in which the flow rate at which the at least one fluid is to be delivered and the volume of the at least one fluid to be delivered are fixed.

Clause 3. The fluid injector system according to clause 1 or 2, wherein the at least one fluid to be delivered during the variable single phase test injection is saline.

Clause 4. The fluid injector system according to any of clauses 1-3, wherein the at least one fluid to be delivered during at least one phase of the multi-phase test injection is saline.

Clause 5. The fluid injector system according to any of clauses 1-4, wherein, for the variable single phase test injection, a volume of the at least one fluid to be delivered is selectable prior to performance of the variable single phase test injection.

Clause 6. The fluid injector system according to any of clauses 1-5, wherein, for the multi-phase test injection, a volume of the at least one fluid to be delivered is selectable prior to performance of the multi-phase test injection.

Clause 7. The fluid injector system according to any of clauses 1-6, wherein, for the multi-phase test injection, a volume of the at least one fluid to be delivered is different for each phase of the multi-phase test injection.

Clause 8. The fluid injector system according to any of clauses 1-7, wherein, for the multi-phase test injection, the flow rate at which the at least one fluid is to be delivered is different for each phase of the multi-phase test injection.

Clause 9. The fluid injector system according to any of clauses 1-8, wherein the flow rate at which the at least one fluid is to be delivered during performance of the variable single phase test injection is varied by varying a speed of the at least one drive member.

Clause 10. The fluid injector system according to any of clauses 1-9, wherein the speed of the at least one drive member is varied via manual input using a control element.

Clause 11. The fluid injector system according to any of clauses 1-10, wherein the control element is one or more buttons or a dial.

Clause 12. The fluid injector system according to any of clauses 1-11, wherein the programming system is further configured to enable adjusting the flow rate at which the at least one fluid is to be delivered during the at least one diagnostic injection phase based on a desired flow rate determined during performance of the variable single phase test injection.

Clause 13. The fluid injector system according to any of clauses 1-12, wherein the multi-phase test injection comprises at least a first phase having a first flow rate and a second phase following the first phase, the second phase having a second flow rate.

Clause 14. The fluid injector system according to any of clauses 1-13, wherein the second flow rate is different from the first flow rate.

Clause 15. The fluid injector system according to any of clauses 1-14, wherein the second flow rate is higher than the first flow rate.

Clause 16. The fluid injector system according to any of clauses 1-15, wherein the test injection procedure and the at least one diagnostic injection procedure define an overall injection protocol.

Clause 17. A computer program product for enabling programming of a test injection procedure to be performed using a fluid injector system prior to a diagnostic injection procedure, the computer program product comprising at least one non-transitory computer-readable medium comprising one or more instructions that, when executed by at least one processor, cause the at least one processor to: enable a user, via the fluid injector system, to select the test injection procedure to be performed from one of a variable single phase test injection and a multi-phase test injection such that upon selecting: (a) the variable single phase test injection, the flow rate at which the at least one fluid is to be delivered during the variable single phase test injection is selectable prior to performance of the variable single phase test injection and may be varied during performance of the variable single phase test injection; and (b) the multi-phase test injection, the flow rate at which the at least one fluid is to be delivered during the multi-phase test injection is selectable for each phase of the multi-phase test injection prior to performance of the multi-phase test injection.

Clause 18. The computer program product according to clause 17, wherein the one or more instructions, when executed by at least one processor, further cause the at least one processor to enable the user, via the fluid injector system, to select a fixed single phase test injection such that, upon selecting the fixed single phase test injection, a flow rate at which at least one fluid is to be delivered during the fixed single phase test injection and a volume of the at least one fluid to be delivered during the fixed single phase test injection are fixed.

Clause 19. The computer program product according to clause 17 or 18, wherein the at least one fluid to be delivered during the variable single phase test injection is saline.

Clause 20. The computer program product according to any of clauses 17-19, wherein the at least one fluid to be delivered during at least one phase of the multi-phase test injection is saline.

Clause 21. The computer program product according to any of clauses 17-20, wherein, for the variable single phase test injection, a volume of the at least one fluid to be delivered is selectable prior to performance of the variable single phase test injection.

Clause 22. The computer program product according to any of clauses 17-21, wherein, for the multi-phase test injection, a volume of the at least one fluid to be delivered is selectable prior to performance of the multi-phase test injection.

Clause 23. The computer program product according to any of clauses 17-22, wherein, for the multi-phase test injection, a volume of the at least one fluid to be delivered is different for each phase of the multi-phase test injection.

Clause 24. The computer program product according to any of clauses 17-23, wherein, for the multi-phase test injection, the flow rate at which the at least one fluid is to be delivered is different for each phase of the multi-phase test injection.

Clause 25. The computer program product according to any of clauses 17-24, wherein the flow rate at which the at least one fluid is to be delivered during performance of the variable single phase test injection is varied by varying a speed of the at least one drive member.

Clause 26. The computer program product according to any of clauses 17-25, wherein the speed of the at least one drive member is varied via manual input using a control element.

Clause 27. The computer program product according to any of clauses 17-26, wherein the control element is one or more buttons or a dial.

Clause 28. The computer program product according to any of clauses 17-27, wherein the one or more instructions, when executed by at least one processor, are further configured to enable adjusting the flow rate at which the at least one fluid is to be delivered during the at least one diagnostic injection phase based on a desired flow rate determined during performance of the variable single phase test injection.

Clause 29. The computer program product according to any of clauses 17-28, wherein the multi-phase test injection comprises at least a first phase having a first flow rate and a second phase following the first phase, the second phase having a second flow rate.

Clause 30. The computer program product according to any of clauses 17-29, wherein the second flow rate is different from the first flow rate.

Clause 31. The computer program product according to any of clauses 17-30, wherein the second flow rate is higher than the first flow rate.

Clause 32. The computer program product according to any of clauses 17-31, wherein the test injection procedure and the at least one diagnostic injection procedure define an overall injection protocol.

Clause 33. A computer-implemented method for performing a test injection procedure using a fluid injector system having at least one drive member by which at least one fluid contained within at least one fluid container is injectable into a patient, the method comprising: driving the at least one drive member, using at least one processor, at a first drive rate to deliver the at least one fluid at a first flow rate; and varying the first drive rate to a second drive rate different from the first drive rate to vary the flow rate at which the at least one fluid is delivered from the first flow rate to a second flow rate different from the first flow rate, wherein varying the first drive rate to the second drive rate comprises one of: (a) receiving user input during a variable single phase test injection, via a control element operatively connected to the at least one processor; and (b) advancing, using the at least one processor, to a next test injection phase of a multi-phase test injection, the next test injection phase comprising the second drive rate.

Clause 34. The computer-implemented method according to clause 33, wherein the second drive rate is higher than the first drive rate.

Clause 35. The computer-implemented method according to clause 33 or 18, wherein the second drive rate is lower than the first drive rate.

Clause 36. The computer-implemented method according to any of clauses 33-34, further comprising selecting, using the at least one processor, a volume of the at least one fluid to be delivered prior to driving the at least one drive member.

Clause 37. The computer-implemented method according to any of clauses 33-36, further comprising selecting, using the at least one processor, the first drive rate prior to driving the at least one drive member.

Clause 38. The computer-implemented method according to any of clauses 33-37, further comprising performing a diagnostic injection procedure following the test injection procedure, the diagnostic injection procedure comprising at least one diagnostic injection phase according to which the at least one fluid is to be injected into the patient so as to effect enhancement of at least one region of interest thereof over a scan duration of a diagnostic imaging procedure.

Clause 39. The computer-implemented method according to any of clauses 33-38, wherein a flow rate at which the at least one fluid is to be injected during the at least one diagnostic injection phase is based on a desired flow rate determined during performance of the test injection procedure.

These and other features and characteristics of the systems, computer program products, and methods for testing acceptability of blood vessel access using a powered fluid injector, as well as the methods of operation and functions of the related elements of structures and the combination of parts and economies of manufacture, will become more apparent upon consideration of the following description and the appended claims with reference to the accompanying drawings, all of which form a part of this specification. It is to be expressly understood, however, that the drawings are for the purpose of illustration and description only.

BRIEF DESCRIPTION OF THE DRAWINGS

In FIGS. 1-10, like reference numerals refer to like elements, unless noted otherwise.

DETAILED DESCRIPTION

Figure 1:
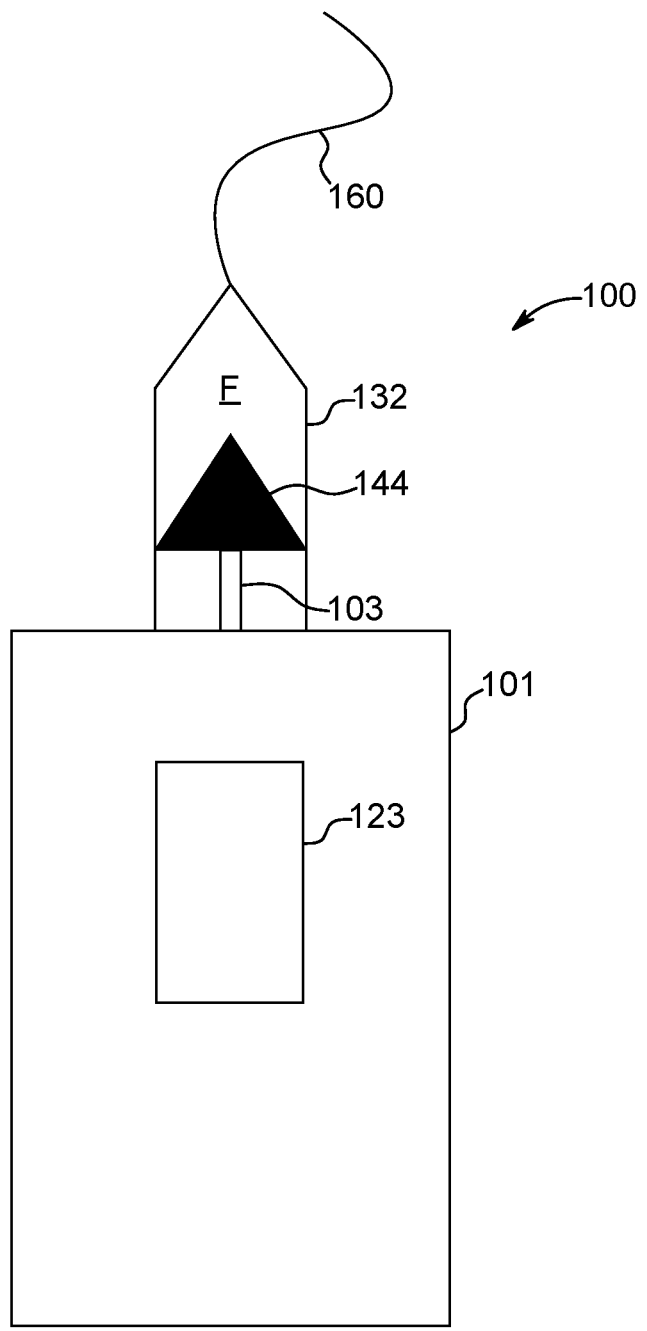
FIG. 1 is a schematic view of a powered fluid injector system in accordance with some examples or aspects of the present disclosure.

The illustrations generally show preferred and non-limiting examples or aspects of the systems and methods of the present disclosure. While the description presents various examples or aspects of the devices, it should not be interpreted in any way as limiting the disclosure. Furthermore, modifications, concepts, and applications of the disclosure's examples or aspects are to be interpreted by those skilled in the art as being encompassed by, but not limited to, the illustrations and descriptions herein.

The following description is provided to enable those skilled in the art to make and use the described examples or aspects contemplated for carrying out the disclosure. Various modifications, equivalents, variations, and alternatives, however, will remain readily apparent to those skilled in the art. Any and all such modifications, variations, equivalents, and alternatives are intended to fall within the spirit and scope of the present disclosure.

For purposes of the description hereinafter, the terms "upper", "lower", "right", "left", "vertical", "horizontal", "top", "bottom", "lateral", "longitudinal", and derivatives thereof shall relate to the disclosure as it is oriented in the drawing figures. When used in relation to a fluid path set, the term "proximal" refers to a portion of a fluid path set on line nearest to a powered fluid injector. When used in relation to a fluid path set, the term "distal" refers to a portion of a fluid path set nearest to an injection site on a patient. When used in relation to a fluid path set or a syringe of a powered fluid injector, the term "radial" refers to a direction in a cross-sectional plane normal to a longitudinal axis of a syringe or an administration line. When used in relation to a fluid path set or a syringe of a powered fluid injector, the term "circumferential" refers to a direction around an inner or outer surface of a sidewall of a syringe or an administration line. When used in relation to a fluid path set or a syringe of a powered fluid injector, the term "axial" refers to a direction along a longitudinal axis of a syringe or a fluid path set extending between the proximal and distal ends.

As used herein with respect to an injection procedure, the term "protocol" refers to a group of parameters such as flow rate, volume injected, duration, etc. that define the amount of fluid(s) to be delivered to a patient during an injection procedure. Such parameters can change over the course of the injection procedure. As used herein, the term "phase" refers generally to a group of parameters that define the amount of fluid(s) to be delivered to a patient during a period of time (or phase duration) that can be less than the total duration of the injection procedure. Thus, the parameters of a phase provide a description of the injection over a time instance corresponding to the time duration of the phase. An injection protocol for a particular injection procedure can be, for example, a single phase, or two or more phases (multi-phase).

As used herein, the term "at least one of" is synonymous with "one or more of". For example, the phrase "at least one of A, B, and C" means any one of A, B, and C, or any combination of any two or more of A, B, and C. For example, "at least one of A, B, and C" includes one or more of A alone; or one or more B alone; or one or more of C alone; or one or more of A and one or more of B; or one or more of A and one or more of C; or one or more of B and one or more of C; or one or more of all of A, B, and C. Similarly, as used herein, the term "at least two of" is synonymous with "two or more of". For example, the phrase "at least two of D, E, and F" means any combination of any two or more of D, E, and F. For example, "at least two of D, E, and F" includes one or more of D and one or more of E; or one or more of D and one or more of F; or one or more of E and one or more of F; or one or more of all of D, E, and F.

It is also to be understood that the specific devices and processes illustrated in the attached drawings and described in the following specification are simply exemplary aspects of the disclosure. Hence, specific dimensions and other physical characteristics related to the examples disclosed herein are not to be considered as limiting.

Although the present invention is described herein primarily in the context of the MEDRAD® Centargo CT Injection System, it will be apparent to persons of ordinary skill in the art that the present invention can be applied to a wide variety of injection systems. Examples of such injection systems include the MEDRAD® Stellant CT Injection System, the MIEDRAD® Stellant FLEX CT Injection System and the MIEDRAD® MRXperion MR Injection System, all of which offered by Bayer HealthCare LLC; the ulrichINJECT CT Motion™ CT Contrast Media Injector offered by ulrich medical; and the CT Exprés® 3D Contrast Media Delivery System offered by Bracco Diagnostics Inc.

Referring to the drawings in which like reference characters refer to like parts throughout the several views thereof, the present disclosure is generally directed to a powered fluid injector system 100 (hereinafter "fluid injector system 100") configured for testing acceptability of blood vessel access via an adjustment of fluid delivery rate during a test injection and/or a plurality of test injection phases, as described herein. Generally, the fluid injector system 100 has a powered injector administrator or device and a fluid delivery set intended to be associated with the injector to deliver one or more fluids from one or more multi-dose containers under pressure into a patient, as described herein. The various devices, components, and features of the fluid injector system 100 and the fluid delivery set associated therewith are likewise described in detail herein.

With reference to FIG. 1, the fluid injector system 100 has at least one reservoir 132 in fluid connection with a fluid path set 160. The at least one reservoir 132 is configured to be filled with at least one fluid F, such as contrast media, saline solution, or any desired medical fluid. The at least one fluid F from the at least one reservoir 132 can be delivered to a patient using the fluid path set 160. The at least one reservoir 132 may be pre-filled or it may have the ability to be filled with the at least one fluid. The at least one reservoir 132 may be at least one syringe, at least one rolling diaphragm syringe, at least one bottle, or at least one collapsible bag.

The system 100 further includes a fluid injector 101, such as an automated or powered fluid injector, that is configured to deliver the fluid F from the at least one reservoir 132 to a patient using the fluid path set 160. For example, the injector 101 may be configured to drive a plunger 144 of the at least one reservoir 132 with a drive member 103, such as a piston, to deliver the fluid F from the at least one fluid reservoir 132 via the fluid path set 160. The at least one drive member 103 may be reciprocally operable to selectively fill the at least one reservoir 132 or deliver fluid from the at least one reservoir 132. In some examples or aspects, the injector 101 may be configured to releasably receive the at least one reservoir 132. The injector 101 may be a multi-syringe injector, wherein several syringes may be oriented side-by-side or in another spatial relationship and are separately actuated by respective pistons associated with the injector 101.

With continued reference to FIG. 1, fluid flow from the at least one reservoir 132 may be regulated by a fluid control module or controller 123 that is configured to operates various valves, stopcocks, and flow regulating structures to regulate the delivery of the at least one fluid F to the patient based on user selected injection parameters, such as injection flow rate, duration, and total injection volume. The controller 123 is generally configured to perform various functions, those of which have the ability to aid in testing acceptability of blood vessel access via an adjustment of fluid delivery rate during a test injection procedure and/or a plurality of test injection phases during a test injection procedure, as described herein.

Figure 2A:
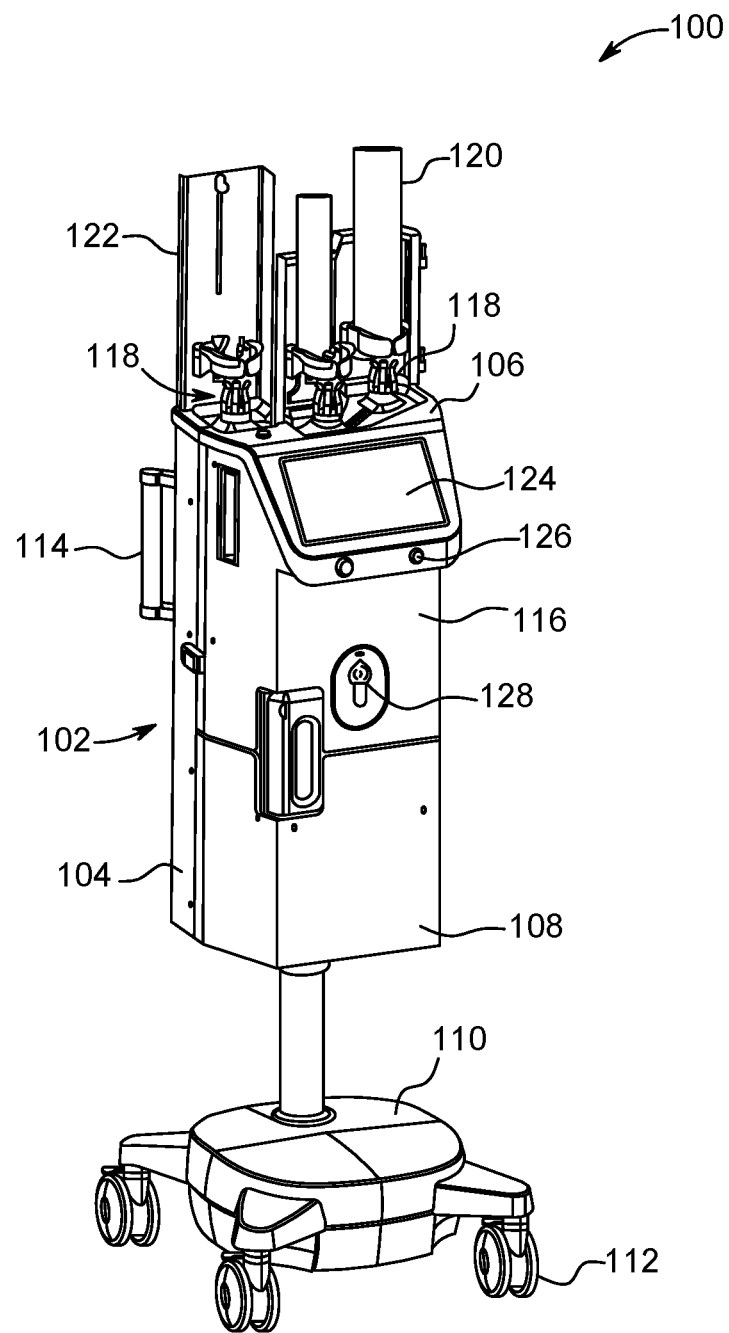
FIG. 2A is a perspective view of a powered fluid injector system in accordance with further examples or aspects of the present disclosure.

With reference to FIG. 2A, the fluid injector system 100 is shown in accordance with some examples or aspects of the present disclosure. The fluid injector system 100 includes the fluid injector 101 having an injector housing 102 with opposed lateral sides 104, a distal or upper end 106, and a proximal or lower end 108. The housing 102 may be supported on a base 110 having one or more wheels 112 for rotatable and movable support of the housing 102 on a floor surface. The one or more wheels 112 may be lockable to prevent the housing 102 from inadvertently moving once positioned at a desired location. At least one handle 114 may be provided to facilitate moving and positioning the fluid injector system 100. In other examples or aspects, the housing 102 may be removably or non-removably secured to a fixed surface, such as a floor, ceiling, wall, or other structure. The housing 102 encloses the various mechanical drive components, electrical and power components necessary to drive the mechanical drive components, and control components, such as electronic memory and electronic control devices (hereinafter electronic control device(s)), used to control operation of reciprocally movable drive members, such as drive members 103 (shown in FIG. 3) associated with the fluid injector system 100 described herein. Such drive members 103 may be reciprocally operable via electromechanical drive components such as a ball screw shaft driven by a motor, a voice coil actuator, a rack-and-pinion gear drive, a linear motor, and the like. In some examples or aspects, at least some of the mechanical drive components, electrical and power components, and control components may be provided on the base 110.

Figure 2B:
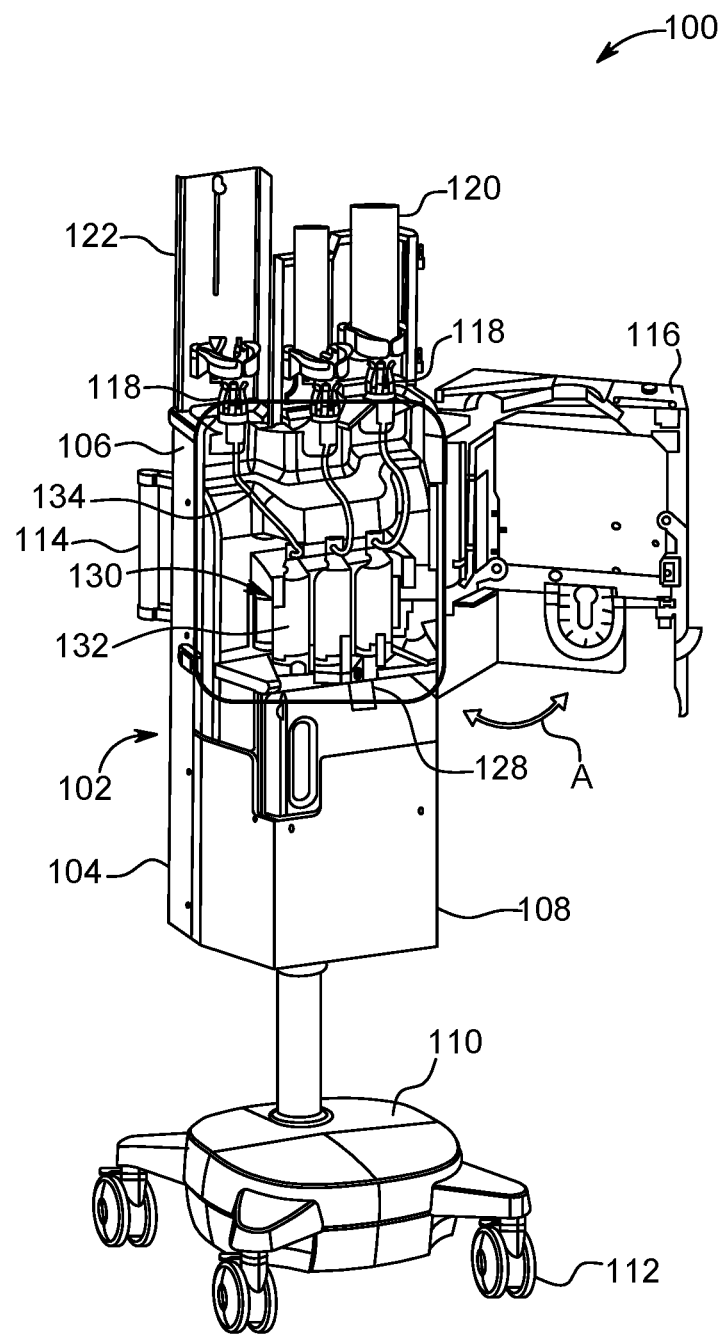
FIG. 2B is a perspective view of the powered fluid injector system of FIG. 2A with an access panel in an open position.

With reference to FIG. 2B, and with continued reference to FIG. 2A, the fluid injector system 100 has at least one door 116 that encloses at least some of the mechanical drive components, electrical and power components, and control components. The door 116 is desirably movable between an open position (shown in FIG. 2B) and a closed position (shown in FIG. 2A) in the direction of arrow A. In some examples or aspects, the door 116 may be lockable.

The fluid injector system 100 further includes at least one bulk fluid connector 118 for connection with at least one bulk fluid source 120. In some examples or aspects, a plurality of bulk fluid connectors 118 may be provided. For example, as shown in FIGS. 2A and 2B, three bulk fluid connectors 118 may be provided in a side-by-side or other arrangement. In some examples or aspects, the at least one bulk fluid connector 118 may be a spike configured for removably connecting to the at least one bulk fluid source 120, such as a vial, bottle, or a bag. The at least one bulk fluid connector 118 may have a reusable or non-reusable interface with each new bulk fluid source 120. The at least one bulk fluid connector 118 may be formed on or attached by tubing with the multi-patient disposable set, as described herein. The at least one bulk fluid source 120 may be configured for receiving a medical fluid, such as saline, an imaging contrast solution, or other medical fluid, for delivery to the fluid injector system 100. The housing 102 may have at least one support member 122 for supporting the at least one bulk fluid source 120 once it is connected to the fluid injector system 100.

The fluid injector system 100 may be operatively associated with the controller 123. The controller 123 may be adapted for controlling the operation of the fluid injector system 100 by allowing the user to manually select the injection parameters, or select a pre-defined injection protocol. In some aspects, the controller 123 may have one or more buttons, knobs, touch pads, displays, switches, dials, or other input and/or output devices to allow the user to user to manually select the injection parameters, or select a pre-defined injection protocol. Alternatively, this functionality may reside with an external control unit or with the fluid injector system 100. In either case, the controller 123 controls, for example but not limited to, the injection pressure, the volumes and flow rates of the various fluids to be delivered to the patient, and/or the ratio of the various fluids to be delivered to the patient.

With reference to FIG. 2A, the fluid injector system 100 includes one or more user interfaces 124, such as a graphical user interface (GUI) display window, for controlling one or more aspects of the fluid injector system 100 via the controller 123. The user interface 124 may display information pertinent to a fluid injection procedure involving the fluid injector system 100, such as current flow rate, fluid pressure, and volume remaining in the at least one bulk fluid source 120 connected to the fluid injector system 100. The user interface 124 may be a touch screen GUI that allows an operator to input commands and/or data for operation of the fluid injector system 100. For example, the one or more buttons, knobs, touch pads, displays, switches, dials, or other input and/or output controls may be manifested as user-selectable regions of the touchscreen GUI to allow the user to manually select the injection parameters or select a pre-defined injection protocol. While the user interface 124 is shown on the injector housing 102, along with the controller 123, in some examples or aspects, the user interface 124 may be a tablet that is detachably connected to the housing 102 and is in wired or wirelessly linked communication with the housing 102.

With continued reference to FIG. 2A, the fluid injector system 100 and/or user interface 124 may include at least one control button 126 for tactile operation by an attendant operator of the fluid injector system 100. In certain examples or aspects, the at least one control button 126 may be part of a keyboard for inputting commands and/or data by the operator. The at least one control button 126 may be hard-wired to the electronic control device(s) associated with the fluid injector system 100 to provide direct input to the electronic control device(s). The at least one control button 126 may also be graphically part of the user interface 124, such as a touch screen. In either arrangement, the at least one control button 126 desirably provides certain individual control features to the attendant operator of the fluid injector system 100, such as but not limited to: (1) inputting information and/or data related to the patient, test injection procedure, and/or diagnostic injection procedure; (2) initiating and/or confirming filling/purging of the fluid injector system 100; and (3) initiating/stopping the test injection procedure or diagnostic injection procedure. As used herein, "test injection procedure" refers to a fluid delivery procedure using the fluid injector system 100 for the purpose of testing the patency of an injection site, while "diagnostic injection procedure" refers to a fluid delivery procedure using the fluid injector system 100 for the purpose of a diagnostic evaluation other than testing the patency of the injection site, such as when delivering contrast during an imaging procedure.

With reference to FIG. 2B, the fluid injector system 100 may have a multi-patient disposable set (MUDS) 130 that is removably connected to the fluid injector system 100 for delivering one or more fluids from the one or more bulk fluid sources 120 to the patient. The MUDS 130 may be configured for delivering fluid using a fluid path set, as described herein. Examples of suitable MUDS 130 and fluid path set configurations for embodiments of the fluid injector system 100 of the present disclosure are described in International Patent Application Publications WO 2016/112163 and WO 2105/106107, the disclosures of each of which are incorporated herein in their entireties by this reference.

The fluid injector system 100 includes at least one slot or connection port 128 (shown in FIG. 2A) for releasably connecting a single-use disposable set to the MUDS 130, as described herein. The MUDS 130 may include one or more fluid reservoirs or syringes 132. In some examples or aspects, the number of syringes 132 may correspond to the number of bulk fluid sources 120. For example, with reference to FIG. 2B, in certain examples or aspects, the MUDS 130 has three syringes 132 in a side-by-side arrangement such that each syringe 132 is fluidly connectable to one of the bulk fluid sources 120. One or more bulk fluid sources 120 may be connected to one or more syringes 132 of the MUDS 130. Each syringe 132 may be fluidly connectable to one of the bulk fluid sources 120 by a corresponding bulk fluid connector 118 and an associated MUDS fluid path 134. The MUDS fluid path 134 may have a spike element that connects to the bulk fluid connector 118. In some examples or aspects, the bulk fluid connector 118 may be provided directly on the MUDS 130.

Figure 3:
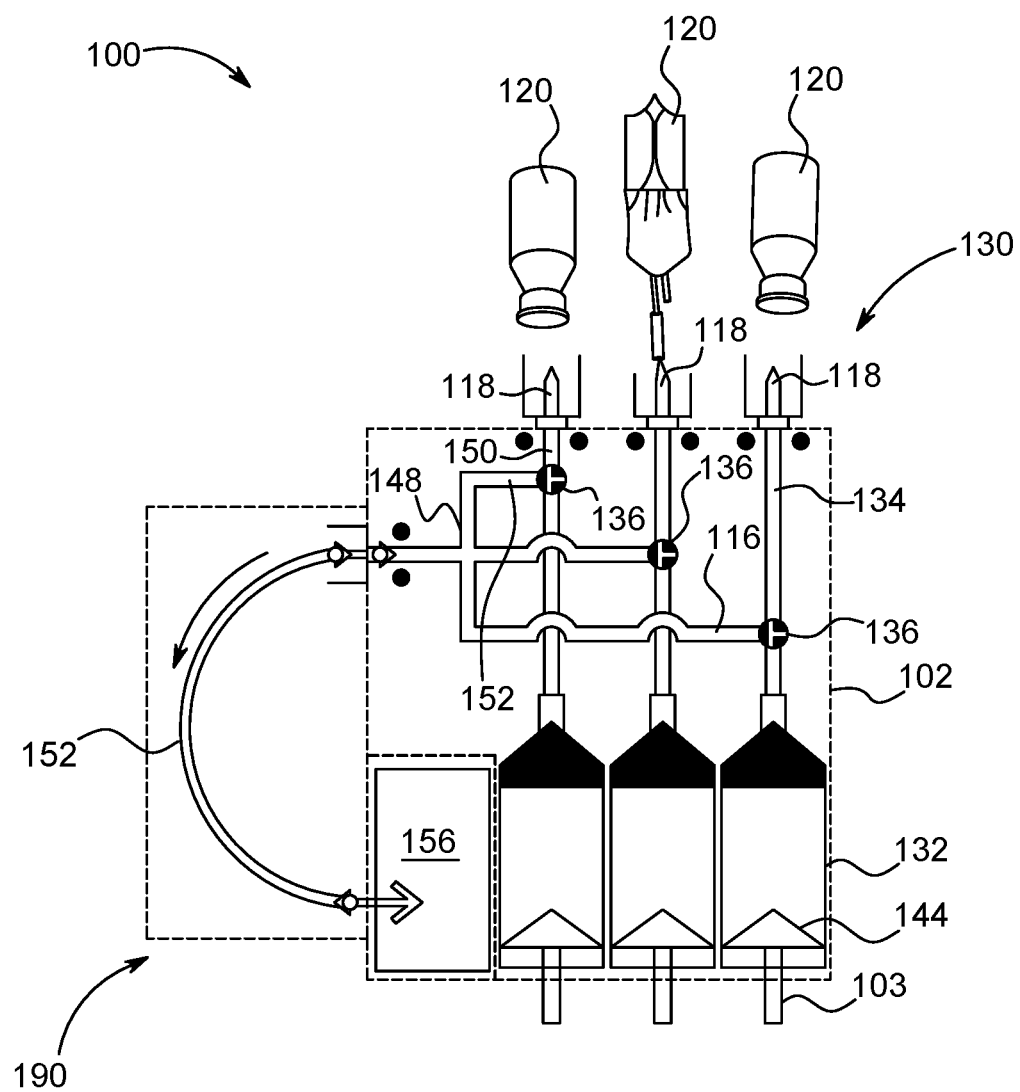
FIG. 3 is a schematic view of various fluid paths within the powered fluid injector system of FIGS. 2A and 2B.

With reference to FIG. 3, each syringe 132 has an elongated, substantially cylindrical syringe body 138 having a front or distal end 140 and a rear or proximal end 142. A syringe plunger 144 is disposed within the syringe body 138 and is reciprocally movable within the syringe body 138 due to movement of a drive member 103 associated with the fluid injector system 100. The distal end 140 of the syringe body 138 is generally conically shaped and tapers to an apex or cone point which is adapted to interface with a corresponding apex curve formed in the recess defined in the fluid injector system 100, as described herein. The syringe apex or cone point is located along a central longitudinal axis L of the syringe body 138. Each syringe 132 has a discharge outlet or conduit 146 at the terminal end of the apex or cone point. The discharge outlet 146 of each syringe 132 is in fluid communication with a valve 136 which provides fluid communication with a manifold 148 and bulk fluid connector 118. The manifold 148 may also provide support for the syringes 132 so that the syringes 132 can be handled as a single, unitary structure. The syringes 132 may be arranged in a side-by-side orientation, or any other orientation that retains the relative positioning of the syringes 132.

With continuing reference to FIG. 3, the one or more valves 136, such as stopcock valves, may be configured for controlling which medical fluid or combinations of medical fluids are withdrawn from the multi-dose bulk fluid source 120 and/or are delivered to a patient through each syringe 132. In some examples or aspects, the one or more valves 136 may be provided on the distal end 140 of the plurality of syringes 132 or on the manifold 148. The manifold 148 may be in fluid communication via the valves 136 and/or the syringes 132 with a first end of the MUDS fluid path 134 that connects each syringe 132 to the corresponding bulk fluid source 120. The opposing second end of the MUDS fluid path 134 may be connected to the respective bulk fluid connector 118 that is configured for fluidly connecting with the bulk fluid source 120.

Depending on the position of the one or more valves 136, fluid may be drawn into the one or more syringes 132, or it may be delivered from the one or more syringes 132. In a first position, such as during the filling of the syringes 132, the one or more valves 136 are oriented such that fluid flows from the bulk fluid source 120 into the desired syringe 132 through a fluid inlet line 150, such as the MUDS fluid path 134. During the filling procedure, the one or more valves 136 are positioned such that fluid flow through one or more fluid outlet lines 152 or the manifold 148 is blocked. In a second position, such as during a fluid delivery procedure, fluid from one or more syringes 132 is delivered to the manifold 148 through the one or more fluid outlet lines 152 or syringe valve outlet ports.

During the fluid delivery procedure, the one or more valves 136 may be positioned such that fluid flow through one or more fluid inlet lines 150 is blocked. In a third position, all fluid flow into and out of the one or more syringes 132 may be blocked, for example by having the one or more valves 136 turned to a position where there is no fluid communication between the interior of the syringe 132 and either the fluid inlet lines 150 or the one or more fluid outlet lines 152/manifold 148. The one or more valves 136, fluid inlet lines 150, and/or fluid outlet lines 152 may be integrated into the manifold 148. The one or more valves 136 may be selectively positioned to the first, second, or third position by manual or automatic handling. For example, the operator may position the one or more valves 136 into the desired position for filling or fluid delivery. In other examples, at least a portion of the fluid injector system 100 is operable for automatically positioning the one or more valves 136 into a desired position for filling or fluid delivery based on input by the operator, as described herein. For example, the operator input may be entered via the user interface 124.

With continued reference to FIG. 3, in some examples or aspects, the fluid outlet line 152 may also be connected to a waste reservoir 156 on the fluid injector system 100. The waste reservoir 156 is desirably separate from the syringes 132 to prevent contamination. In some examples or aspects, the waste reservoir 156 is configured to receive waste fluid expelled from the syringes 132 during, for example, a priming operation. The waste reservoir 156 may be removable from the housing 102 in order to dispose of the contents of the waste reservoir 156. In other examples, the waste reservoir 156 may have a draining port (not shown) for emptying the contents of the waste reservoir 156 without removing the waste reservoir 156 from the housing 102. In some examples or aspects, the waste reservoir 156 is provided as a separate component from the MUDS 130.

Figure 4:
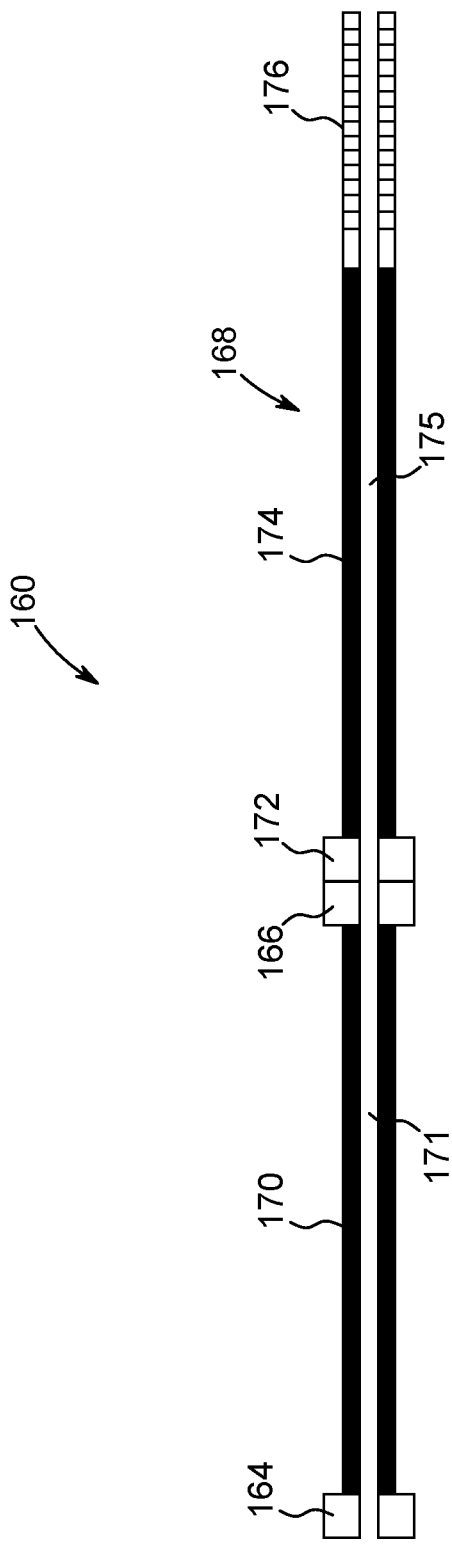
FIG. 4 is a schematic view of a fluid path set in accordance with some examples or aspects of the present disclosure.

With reference to FIG. 4, a fluid path set 160 is shown in accordance with one example or aspect of the present disclosure. The fluid path set 160 is configured for connecting to a connection port 128 (shown in FIG. 2A) on at least a portion of the MUDS 130 and/or the housing 102 of fluid injector system 100. The connection port 128 may be in fluid communication with the fluid outlet line 152 on the MUDS 130. Desirably, the connection between the fluid path set 160 and the connection port 128 is a releasable connection to allow the fluid path set 160 to be selectively disconnected from and connected to the connection port 128. In some examples or aspects, the fluid path set 160 may be disconnected from the connection port 128 and disposed after each fluid delivery procedure and a new fluid path set 160 may be connected to the connection port 128 for a subsequent fluid delivery procedure.

With continued reference to FIG. 4, the fluid path set 160 has a fluid inlet port 164 that is configured for releasable connection with the connection port 128 from which the fluid inlet port 164 receives fluid delivered from the fluid injector system 100. The fluid path set 160 further has a fluid outlet port 166 that is configured for connecting to a vascular access device 168. In some examples or aspects, the fluid outlet port 166 may be a luer-type fitting or other connection mechanism configured for connecting to the vascular access device 168. The fluid inlet port 164 and the fluid outlet port 166 are fluidly connected by first tubing 170 having a first lumen 171.

With continued reference to FIG. 4, in some examples or aspects, the vascular access device 168 may be a peripheral line configured for placement within small blood vessels in an arm or a leg of a patient. In other examples or aspects, the vascular access device 168 may be a central line configured for placement in larger blood vessels of the patient. Examples of various vascular access device 168 include, without limitation, peripheral IV catheters (NV), midline catheters, peripherally inserted central catheters (PICC), central venous catheters (CVC), and implanted ports. In some examples or aspects, the vascular access device 168 may have a connector 172 configured for connecting to the fluid outlet port 166. The vascular access device 168 further has second tubing 174 with a second lumen 175. A distal end 176 of the vascular access device 168 is configured to be positioned within the blood vessel and enable fluid delivery to the blood vessel.

Having described the structure of the fluid injector system 100, an exemplary injection procedure will now be described with reference to FIG. 5. The injection procedure, as performed by the fluid injector system 100, may be enabled by a computer program. The computer program product may include at least one non-transitory computer-readable medium having one or more instructions executable by at least one processor to cause the at least one processor to execute all or part of the injection procedure. In some examples or aspects, the at least one non-transitory computer-readable medium and the at least one processor may include or correspond to the memory 206 and the processor 204, respectively, as will be described later in greater detail with reference to FIG. 10. In some examples or aspects, the injection procedure may be configured as an injection procedure protocol having a group of preselected parameters, such as, for example, the flow rate, volume, and type of fluid to be injected. The injection procedure protocol may have one or more sub-protocols, such as a test injection protocol and a diagnostic injection protocol. Depending on an imaging procedure, a clinician may design an injection procedure protocol having a desired test injection sub-protocol and a desired diagnostic injection sub-protocol. Protocol selection and entry, saving and editing of injection parameters, injection phase information and delays, etc. may be done through the user interface 124 of the fluid injector system 101.

The injection procedure protocol may be set up such that the test injection procedure sub-protocol is performed first, thereby allowing the clinician to verify patency of the injection site. After completion of the test injection procedure sub-protocol, a diagnostic injection procedure sub-protocol may be performed, during which at least one diagnostic injection phase is carried out according to which the at least one fluid is to be injected into the patient so as to effect enhancement of at least one region of interest. In some examples or aspects, the test injection procedure may be performed independently and without being part of an injection procedure protocol. As described herein, the test injection procedure may be configured for assisting a clinician in assuring a proper placement of the needle, the cannula, the catheter, the central line or other vascular access device, as the case may be, in the patient's vasculature to assure that the end thereof is clear (i.e., not clotted or otherwise obstructed), and fully inserted into the blood vessel without perforating the wall.

Figure 5:
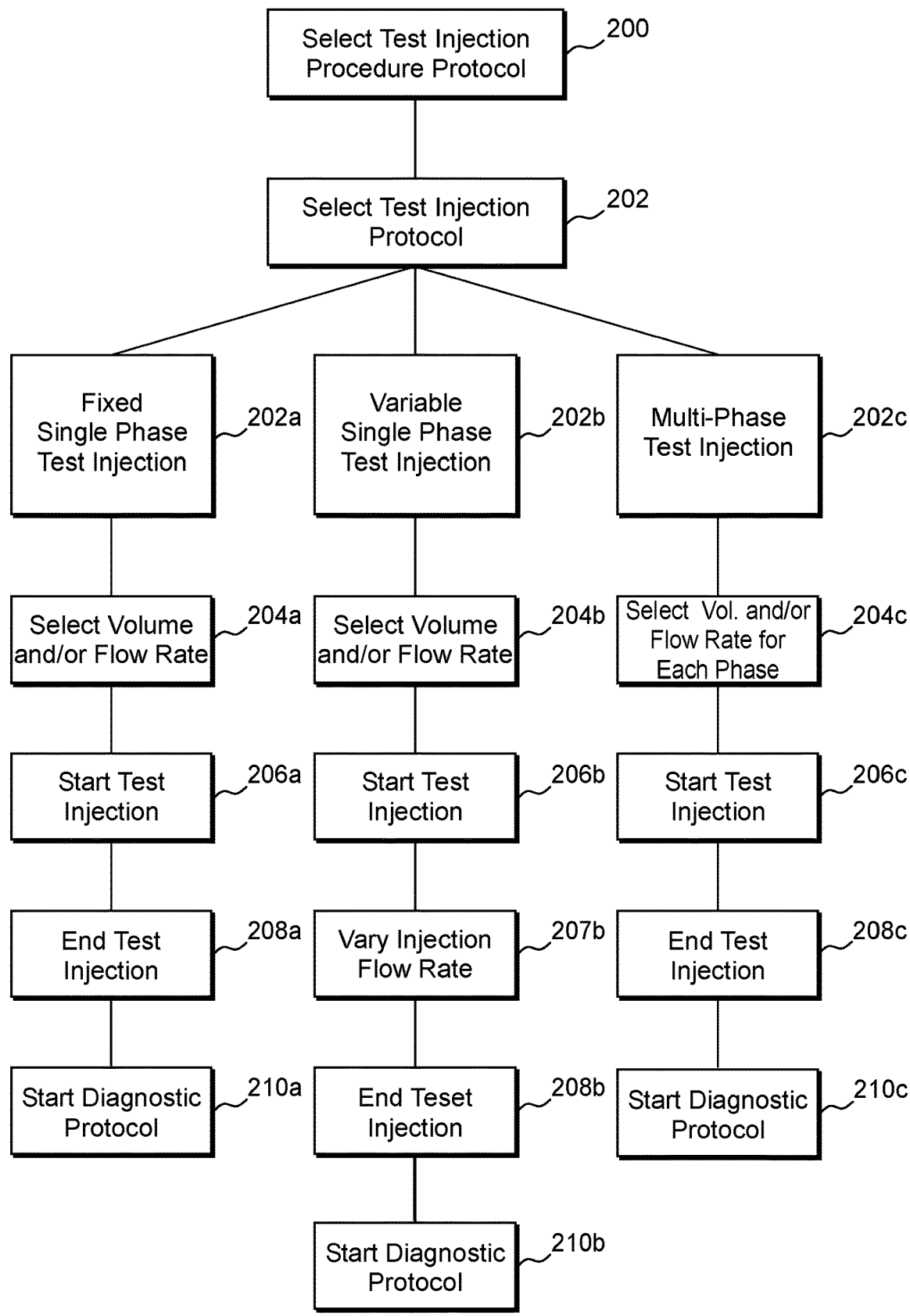
FIG. 5 is a flow chart showing an exemplary injection protocol having a test injection procedure that offers at least two test injection protocols from which to choose, for example, a variable single phase test injection and a multi-phase test injection.

With continued reference to FIG. 5, in step 200, an injection procedure protocol is selected. In some examples or aspects, the injection procedure protocol may be stored in the controller 123 of the fluid injector system 100 as part of a protocol library. A desired injection procedure protocol may be recalled through the user interface 124. In some examples or aspects, selecting a desired injection procedure protocol automatically selects the test injection protocol for that injection procedure. In other examples or aspects, the user may independently select a desired test injection protocol to be performed as part of the overall injection procedure protocol. For example, the test injection procedure may be selected in step 202 by pressing or selecting a button 126 on the housing 102 or the user interface 124. In some examples or aspects, the button 126 may have a label, such as "Test Injection", to indicate that pressing or selecting the button 126 will enable a test injection procedure for performing a patency check. Pressing or selecting the button 126 may display a menu of available commands on the user interface 124 for controlling or editing the test injection protocol.

With continued reference to FIG. 5, at steps 202a, 202b, 202c, one of a plurality of test injection protocols may be selected. In some examples or aspects, selection of the test injection protocol may be done automatically via selection of the overall injection protocol at step 200. In other examples or aspects, the user may independently select a desired test injection protocol. For example, the user interface 124 may present a menu having a plurality of available test injection protocols. The user may choose a desired test injection protocol based on desired fluid, flow rate of the fluid during the test injection procedure, and/or the volume of fluid delivered during the test injection procedure. In some examples or aspects, the user may select one of the following test injection protocols at step 202: (a) a fixed single-phase test injection (202a), (b) a variable single-phase test injection (202b), or (c) a multi-phase test injection (202c).

In a fixed single-phase test injection (202a), the controller 123 controls the fluid injector 101 to deliver a fixed volume of fluid at a target flow rate. With continued reference to FIG. 5, prior to starting a test injection, at step 204a, the user may select at least one of a volume of fluid and a flow rate at which the fluid is to be delivered to the patient during the test injection procedure. In some examples or aspects, the user interface 124 may display suggested volume and/or flow rate values that simulate the test injection conditions to the diagnostic injection procedure that is to follow. The volume and flow rate may be preset and the user may be permitted to modify the preselected values prior to starting the test injection procedure. A volume for the fixed single-phase test injection (202a) may be based on a preset default, or a historical volume used for previous test injection procedures. In some examples or aspects, the volume may be changed prior to initiating the test injection procedure. For example, an interface for adjusting a volume of fluid delivered during the fixed single-phase test injection (202a) may be displayed on the user interface 124 allowing the user to increase or decrease the desired volume of fluid from the preset default by making an appropriate selection on the user interface 124. Similarly, a flow rate for the fixed single-phase test injection (202a) may be based on a preset default, or a historical flow rate used for previous test injection procedures. In some examples or aspects, the flow rate may be changed prior to initiating the test injection procedure. For example, an interface for adjusting a flow rate of fluid delivered during the fixed single-phase test injection (202a) may be displayed on the user interface 124 allowing the user increase or decrease the desired flow rate from the preset default by making an appropriate selection on the user interface 124.

Figure 6:
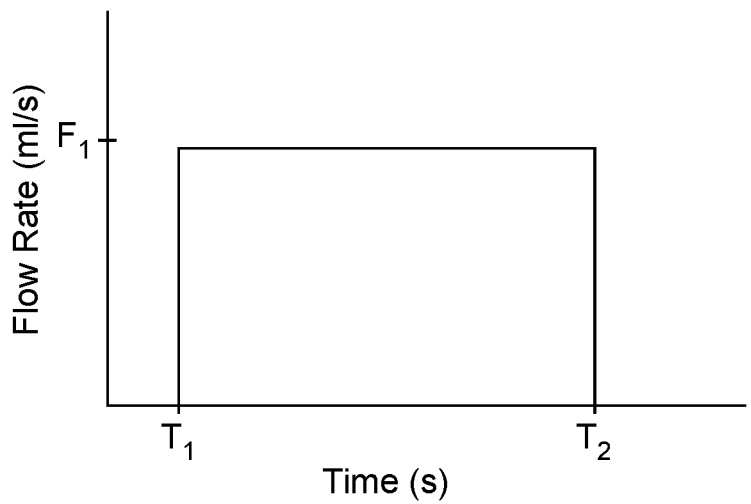
FIG. 6 is a graph of an exemplary test injection procedure showing a fixed flow rate typical of the fixed single phase test injection of FIG. 5.

With continued reference to FIG. 5, after selecting the desired volume and flow rate for a fixed single-phase test injection (202a) at step 204a, the selected fixed single-phase test injection (202a) is executed at step 206a. In this step, fluid F from the at least one reservoir 132 is delivered to the patient via the fluid path set 160 by driving the fluid F from the at least one reservoir 132 using the fluid injector 101. For example, the fixed single-phase test injection (202a) may include an injection of one fluid, such as saline, at the preselected volume and flow rate selected at step 204a. The fixed single-phase test injection (202a) may be initiated by, for example, selecting a button 126 labeled "Start" on the user interface 124. A graph showing the flow rate of a fixed single-phase test injection (202a) as a function of time is shown in FIG. 6. At time $T_1$, which indicates the start of the test injection, the fluid injector 101 quickly ramps up the flow rate to a target flow rate $F_1$. This target flow rate is maintained throughout the test injection until the predetermined volume of fluid is delivered, at which point the test injection terminates at time $T_2$.

During the test injection, the user evaluates the test injection by visually observing and/or palpating the injection site. The user may further observe the quality of the images achieved at the preselected volume and flow rate. At the end of the fixed single-phase test injection (202a), such as when the predetermined volume of fluid is delivered, the fluid injector 101 may automatically terminate the test injection procedure at step 208a. In some examples or aspects, the user may have an option to end the test injection procedure at any time during the test injection by, for example, selecting or pressing a button labeled "End" to cause the fluid injector 101 to stop delivering the fluid. In some examples or aspects, after ending the test injection procedure, a diagnostic injection protocol may start at step 210a. In some examples or aspects, the diagnostic injection protocol at step 210a may include at least one diagnostic injection phase according to which at least one fluid is to be injected into the patient so as to effect enhancement of at least one region of interest thereof over a scan duration of a diagnostic imaging procedure. A flow rate at which the at least one fluid is to be injected during the at least one diagnostic injection phase may be automatically adjusted based on a desired flow rate determined during performance of the test injection procedure at step 206a-208a.

With continued reference to FIG. 5, in a variable single-phase test injection (202b), the controller 123 controls the fluid injector 101 to deliver fluid at a first flow rate and allow a change of the flow rate to a second flow rate during the test injection procedure. In some examples or aspects, the first flow rate may be higher or lower than the second flow rate. The second flow rate may correspond to a rate at which the fluid is to be injected during a diagnostic test procedure. The user may manually increase or decrease the flow rate from the first flow rate to the second flow rate as the test injection progresses. In some examples or aspects, the user may observe a pressure graph on the fluid injector system 100 during the variable single-phase test injection and increase or decrease the flow rate based on the output of the pressure graph.

Prior to starting a test injection, at step 204b, the user may select at least one of a volume of fluid and the first flow rate at which the fluid is to be delivered to the patient at the start of the test injection procedure. The volume and first flow rate may be preset and the user may be permitted to modify the preselected values prior to starting the test injection procedure. A volume for the variable single-phase test injection (202b) may be based on a preset default, or a historical volume used for previous test injection procedures. In some examples or aspects, the volume may be changed prior to initiating the test injection procedure. For example, an interface for adjusting a volume of fluid delivered during the variable single-phase test injection (202b) may be displayed on the user interface 124 allowing the user to increase or decrease the desired volume of fluid from the preset default by making an appropriate selection on the user interface 124. Similarly, the first flow rate for the variable single-phase test injection (202b) may be based on a preset default, or a historical flow rate used for previous test injection procedures. In some examples or aspects, the first flow rate may be changed prior to initiating the test injection procedure. For example, an interface for adjusting the first flow rate of fluid delivered during the variable single-phase test injection (202b) may be displayed on the user interface 124 allowing the user increase or decrease the desired first flow rate from the preset default by making an appropriate selection on the user interface 124.

After selecting the desired volume and first flow rate for the variable single-phase test injection (202b), the selected variable single-phase test injection (202b) is executed at step 206b. In this step, fluid F from the at least one reservoir 132 is delivered to the patient via the fluid path set 160 by driving the fluid F from the at least one reservoir 132 using the fluid injector 101. For example, the variable single-phase test injection (202a) may include an injection of one fluid, such as saline, at the preselected volume and first flow rate selected at step 204b. The variable single-phase test injection (202b) may be initiated by, for example, selecting a button 126 labeled "Start" on the user interface 124.

Figure 9A:
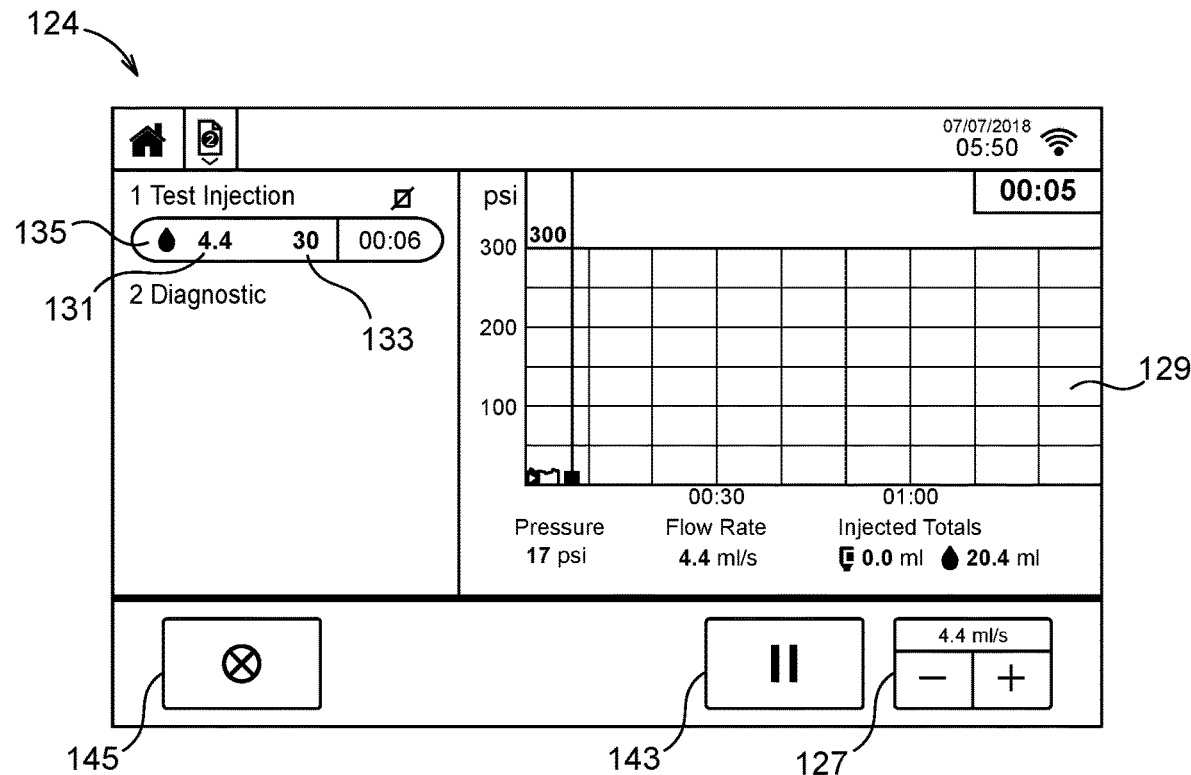
FIG. 9A is an exemplary user interface for a variable single phase test injection.

During the test injection, the user evaluates the test injection by visually observing and/or palpating the injection site. At step 207b, the user may choose to adjust or vary the flow rate of fluid from the first flow rate to the second or target flow rate as the fluid is delivered. For example, the user may increase or decrease the flow rate from the first flow rate to the second flow rate. In some examples or aspects, such as shown in FIG. 9A, an interface for adjusting the flow rate during the test injection may be displayed on the user interface 124 to allow the user to increase or decrease the desired flow rate from the first flow rate by making an appropriate selection on the user interface 124. For example, as shown in FIG. 9A, the user interface 124 may have a control element 127 for increasing or decreasing the flow rate during the test injection. While FIG. 9A shows the control element 127 as buttons displayed on user interface 124, the control element 127 may be a physical element. The user may further observe a pressure graph 129 on the user interface 124 at the first flow rate. Increasing or decreasing the flow rate through the user interface 124 during the test injection has a corresponding effect on the pressure graph 129, thereby allowing the user to determine an optimal flow rate to be used during the diagnostic injection procedure. In other words, live adjustment of the flow rate can be performed based on observed feedback from the injection site, the pressure graph 129, and the patient's reaction.

With reference to FIG. 9A, region 131 of the user interface 124 identifies the flow rate of the variable single-phase protocol, while region 133 identifies a volume of fluid to be delivered. Region 135 identifies the type of fluid to be delivered. Typically, saline is used for the test injection because severity of a saline infiltration into the patient's tissue if the injection site is not patent is less severe than if contrast is used. Prior to starting the test injection procedure, the user may alter these parameters by pushing any of these regions, to switch thereby to a protocol editing mode or user interface. In this mode/user interface, the user may change and store the flow rate, volume, and type of fluid to a desired flow rate, volume, and type of fluid. The user interface 124 may further have a control 143 for pausing the injection and a control 145 for stopping the injection.

In other examples or aspects, the fluid injector 101 may have one or more physical buttons 126 or dials for adjusting the flow rate during the test injection. In some examples, the user may make a plurality of adjustments to the flow rate from the first flow rate. For example, the user may initially increase (or decrease) the flow rate from the first flow rate to the second flow rate, followed by one or more flow rate adjustments from the second flow rate. In some examples or aspects, the user may continue increasing (or decreasing) the flow rate until the pressure graph 129 indicates a desired pressure value. At the end of the variable single-phase test injection (202b), the fluid injector 101 may automatically terminate the test injection procedure at step 208b. In some examples or aspects, the user may have an option to end the test injection procedure at any time during the test injection by, for example, selecting or pressing a button labeled "End" to cause the fluid injector 101 to stop delivering the fluid. In some examples or aspects, after ending the test injection procedure, a diagnostic injection protocol may start at step 210b. In some examples or aspects, the diagnostic injection protocol at step 210b may include at least one diagnostic injection phase according to which at least one fluid is to be injected into the patient so as to effect enhancement of at least one region of interest thereof over a scan duration of a diagnostic imaging procedure. A flow rate at which the at least one fluid is to be injected during the at least one diagnostic injection phase may be automatically adjusted based on a desired flow rate determined during performance of the test injection procedure at step 206b-208b.

Depending on the outcome of the test injection procedure, the user may adjust the injection parameters of the diagnostic injection procedure. For example, the user may adjust a pre-programmed flow rate of the diagnostic injection procedure, such as by increasing or lowering the flow rate, based on observations made during the test injection procedure, such as the output of the pressure graph.

Figure 7:
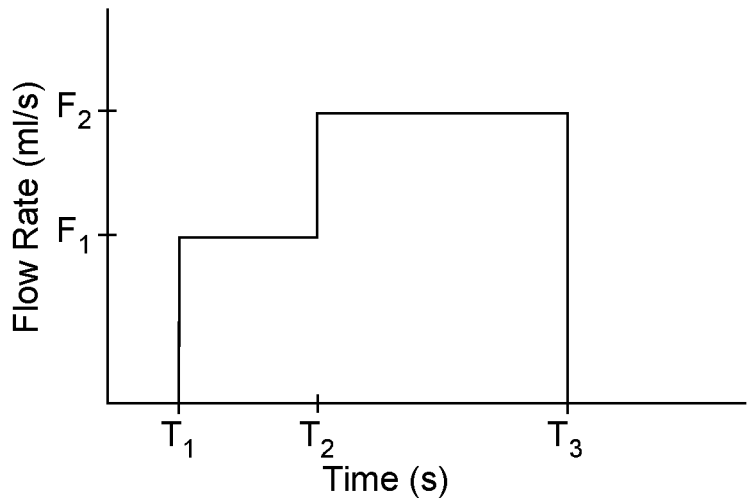
FIG. 7 is a graph of an exemplary test injection procedure showing an adjustment in fluid flow rate as a function of time typical of the variable single phase test injection of FIG. 5.

An exemplary graph showing the flow rate of the variable single-phase test injection (202b) as a function of time is shown in FIG. 7. At time $T_1$, which indicates the start of the test injection, the fluid injector 101 quickly ramps up the flow rate to a first flow rate $F_1$. During the course of the test injection, the user may increase the flow rate from the first flow rate $F_1$ to a second or target flow rate $F_2$ at time $T_2$. While FIG. 7 shows the second or target flow rate $F_2$ being higher than the first flow rate $F_1$, the second or target flow rate $F_2$ may be lower than the first flow rate $F_1$. Additionally, while each flow rate is shown as having the same duration, the duration of each flow rate may be varied. Furthermore, while FIG. 7 shows a change from the first flow rate $F_1$ to the second or target flow rate $F_2$ as a step function, this change can be accomplished gradually as a ramp function. The test injection terminates at time $T_3$.

With reference to FIG. 5, in a multi-phase test injection (202c), the controller 123 controls the fluid injector 101 to deliver one or more fluids in a plurality of phases. The plurality of phases may be saved in the controller 123 as a test injection protocol. Prior to starting a test injection, the user may select one from a plurality of stored multi-phase test injection protocols. Each multi-phase test injection protocol has at least two phases, with each phase defining a flow rate and duration (i.e., volume to be injected). Each phase may have a preset volume and flow rate. In some examples or aspects, each phase may have a progressively higher programmed flow rate.

In some examples or aspects, at step 204c, the user may be permitted to modify the preselected values for each phase prior to starting the test injection procedure. In some examples or aspects, the user may define a new test injection protocol by selecting a desired fluid, flow rate, and volume to be delivered at each phase of the multi-phase test injection. The multi-phase test injection (202c) may use one or more fluids. For example, the multi-phase test injection (202c) may use contrast media and saline, with an injection of the contrast media followed by a saline flush, or a bolus of contrast media may be surrounded by slugs of saline. In further examples, the multi-phase test injection (202c) may be done only with contrast media or only with saline.

Figure 9B:
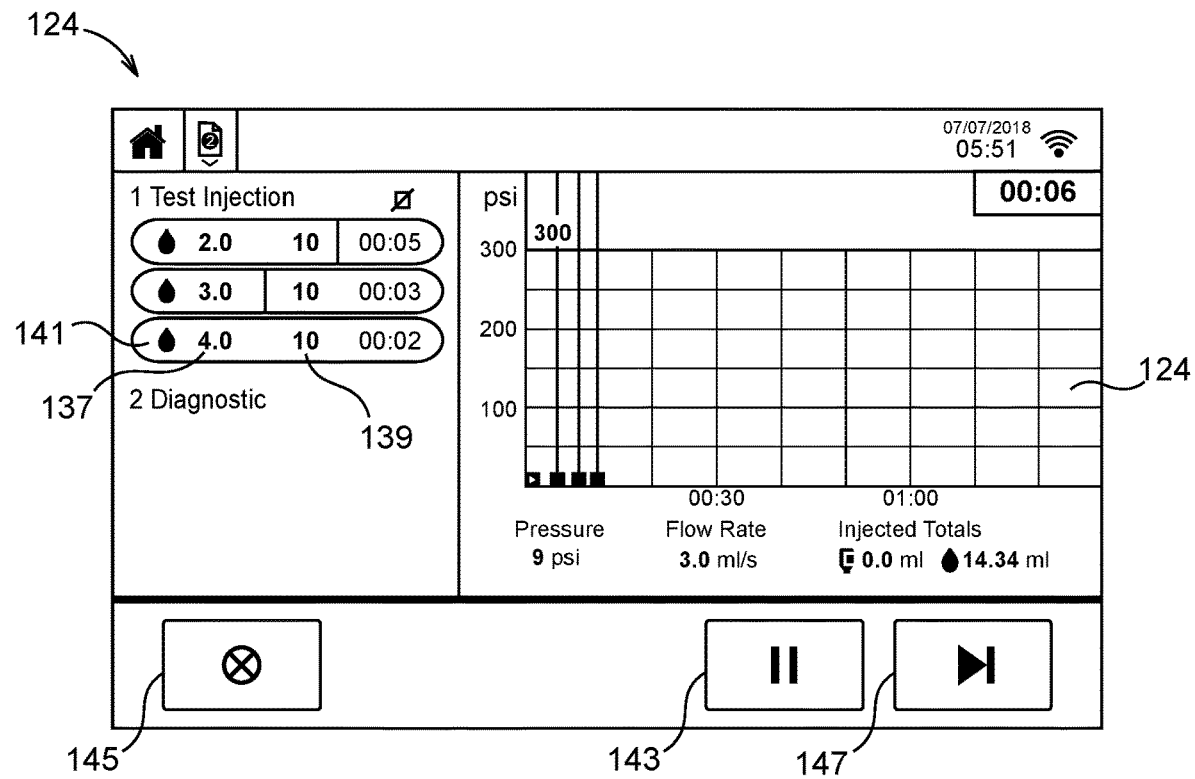
FIG. 9B is an exemplary user interface for a multi-phase test injection.

With reference to FIG. 9B, the user interface 124 may have a region 137 that identifies the flow rate for each phase of the multi-phase test injection protocol, while region 139 identifies a volume of fluid to be delivered during each phase. Region 141 identifies the type of fluid to be delivered for each phase. Prior to starting the multi-phase test injection procedure, the user may alter these parameters by pushing any of these regions, to switch thereby to a protocol editing mode or user interface. In this mode/user interface, the user may change and store the flow rate, volume, and type of fluid to a desired flow rate, volume, and type of fluid for each phase of the multi-phase test injection protocol. The user interface 124 may further have controls for starting the injection 147, pausing the injection 143, and stopping the injection 145.

After selecting the desired multi-phase test injection (202c), the selected multi-phase test injection (202c) is executed at step 206c. In this step, fluid F from at least one reservoir 132 is delivered to the patient via the fluid path set 160 by driving the fluid F from the at least one reservoir 132 using the fluid injector 101. The multi-phase test injection (202c) may be initiated by, for example, selecting a button 126 labeled "Start" on the user interface 124.

During the test injection, the user evaluates the test injection by visually observing and/or palpating the injection site. The user may further observe the quality of the images achieved at various phases of the selected multi-phase protocol. At the end of the multi-phase test injection (202c), the fluid injector 101 may automatically terminate the test injection procedure at step 208c. In some examples or aspects, the user may have an option to end the test injection procedure at any time during the test injection by, for example, selecting or pressing a button labeled "End" to cause the fluid injector 101 to stop delivering the fluid.

Figure 8:
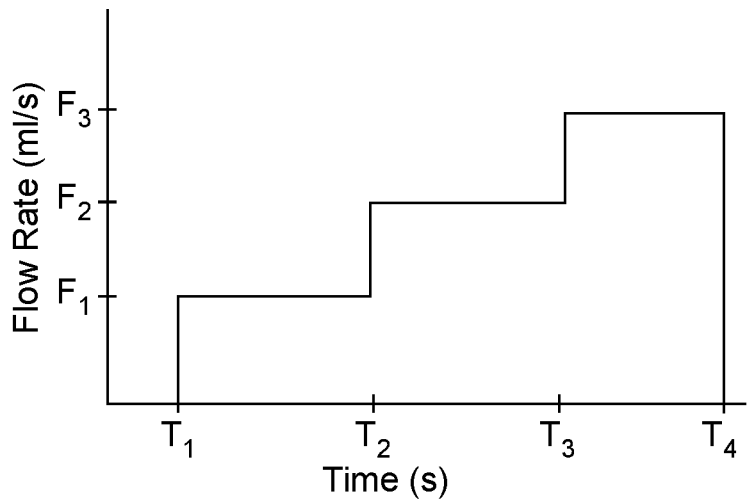
FIG. 8 is a graph of an exemplary test injection procedure showing a plurality of test injection phases typical of the multi-phase test injection of FIG. 5.

An exemplary graph showing the flow rate of the multi-phase test injection (202c) as a function of time is shown in FIG. 8. While a three-phase protocol is shown using a single fluid, other test injection protocols may have fewer or more phases with one or more fluids. At time $T_1$, which indicates the start of a first phase of the test injection, the fluid injector 101 quickly ramps up the flow rate of a first fluid to a first flow rate $F_1$. At the end of the first phase at time $T_2$, the first flow rate $F_1$ may be automatically increased to a second flow rate $F_2$ during the second phase. While FIG. 8 shows the second flow rate $F_2$ being higher than the first flow rate $F_1$, the second flow rate $F_2$ may be lower than the first flow rate $F_1$. At the end of the second phase at time $T_3$, the second flow rate $F_2$ may be automatically increased to a third flow rate $F_3$ during the third phase. The third flow rate $F_3$ may be a target flow rate. While FIG. 8 shows the third flow rate $F_3$ being higher than the second flow rate $F_2$, the third flow rate $F_3$ may be lower than the second flow rate $F_2$. Additionally, while each flow rate is shown as having the same duration, the duration of each flow rate may be varied. Furthermore, while FIG. 8 shows a change from the first flow rate $F_1$ to the second flow rate $F_2$ and from the second flow rate $F_2$ to the third flow rate $F_3$ as step functions, these changes can be implemented gradually as ramp functions. The third phase of the test injection terminates at time $T_4$.

The variable single-phase test injection (202b) and multi-phase test injection (202c) provide several advantages during test injection procedures. Starting the test injection procedure at a lower flow rate that is followed by an increase in flow rate increases patient comfort during the procedure. Because the patient is familiar with how a fluid injection feels at a low flow rate, the patient is less likely to be disturbed by an increase in the flow rate during the same test injection. In variable single-phase test injections, the user can decrease the flow rate if the patient is not comfortable with the high flow rate. Multi-phase test injections provide an ability to allow a complex test injection as a part of the overall injection protocol that can be integrated with a diagnostic protocol, thereby increasing the speed and efficiency of the entire procedure.

Figure 10:
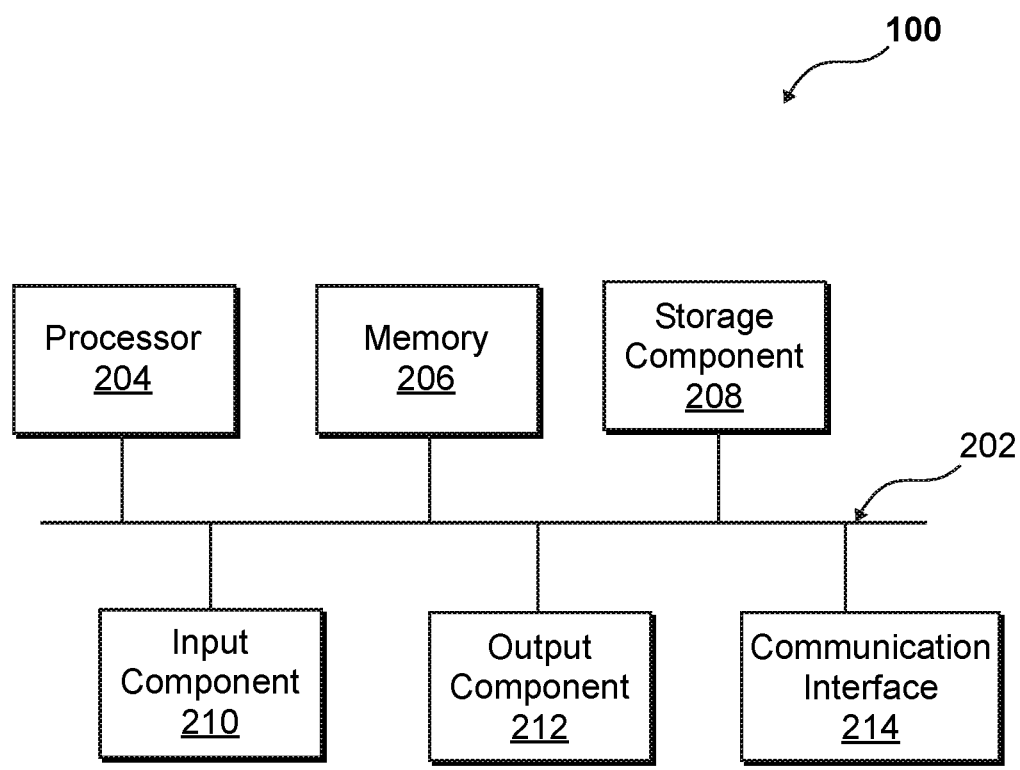
FIG. 10 is a diagram of example components of the powered fluid injector system shown in FIGS. 1, 2A-2B and 3.

Referring now to FIG. 10, FIG. 10 is a diagram of example components of the fluid injector system 100 shown in FIGS. 1, 2A-2B and 3. The components include a bus 202, a processor 204, memory 206, a storage component 208, an input component 210, an output component 212, and a communication interface 214.

Bus 202 may include one or more components that permit communication among the other components shown in FIG. 10. In some non-limiting embodiments or aspects, processor 204 may be implemented in hardware, firmware, or a combination of hardware and software. For example, processor 204 may include a processor (e.g., a central processing unit (CPU), a graphics processing unit (GPU), an accelerated processing unit (APU), etc.), a microprocessor, a digital signal processor (DSP), and/or any processing component (e.g., a field-programmable gate array (FPGA), an application-specific integrated circuit (ASIC), etc.) that can be programmed to perform a function. Memory 206 may include random access memory (RAM), read only memory (ROM), and/or another type of dynamic or static storage device (e.g., flash memory, magnetic memory, optical memory, etc.) that stores information and/or instructions for use by processor 204.

Storage component 208 may store information and/or software related to the operation and use of fluid injector system 100. For example, storage component 208 may include a hard disk (e.g., a magnetic disk, an optical disk, a magneto-optic disk, a solid state disk, etc.), a compact disc (CD), a digital versatile disc (DVD), a floppy disk, a cartridge, a magnetic tape, and/or another type of computer-readable medium, along with a corresponding drive.

Input component 210 may include one or more components that permit fluid injector system 100 to receive information, such as via user interface(s) 124, a keyboard, a keypad, a mouse, a button, a switch, a microphone, etc. Additionally, or alternatively, input component 210 may include a sensor for sensing information (e.g., a global positioning system (GPS) component, an accelerometer, a gyroscope, an actuator, etc.). Output component 212 may include one or more components that provide output information from fluid injector system 100 (e.g., user interface(s) 124, a speaker, one or more light-emitting diodes (LEDs), etc.).

Communication interface 214 may include a transceiver-like component (e.g., a transceiver, a separate receiver and transmitter, etc.) that enables fluid injector system 100 to communicate with other devices, such as via a wired connection, a wireless connection, or a combination of wired and wireless connections. Communication interface 214 may permit fluid injector system 100 to receive information from another device and/or provide information to another device. For example, communication interface 214 may include an Ethernet interface, an optical interface, a coaxial interface, an infrared interface, a radio frequency (RF) interface, a universal serial bus (USB) interface, a WiFi® interface, a cellular network interface, and/or the like.

Fluid injector system 100 may perform one or more of the processes described herein. Fluid injector system 100 may perform these processes based on processor 204 executing software instructions stored by a computer-readable medium, such as memory 206 and/or storage component 208. A computer-readable medium (e.g., a non-transitory computer-readable medium) is defined herein as a non-transitory memory device. A memory device includes memory space located inside of a single physical storage device or memory space spread across multiple physical storage devices.

Software instructions may be read into memory 206 and/or storage component 208 from another computer-readable medium or from another device via communication interface 214. When executed, software instructions stored in memory 206 and/or storage component 208 may cause processor 204 to perform one or more processes described herein. Additionally, or alternatively, hardwired circuitry may be used in place of or in combination with software instructions to perform one or more processes described herein. Thus, embodiments or aspects described herein are not limited to any specific combination of hardware circuitry and software.

The number and arrangement of the components shown in FIG. 10 are provided as an example. In some non-limiting embodiments or aspects, fluid injector system 100 may include additional components, fewer components, different components, or differently arranged components than those shown in FIG. 10. Additionally, or alternatively, a set of components (e.g., one or more components) of fluid injector system 100 may perform one or more functions described as being performed by another set of components of fluid injector system 100.

While several examples or aspects of systems and methods for testing acceptability of blood vessel access using a powered fluid injector are shown in the accompanying drawings and described hereinabove in detail, other examples or aspects will be apparent to, and readily made by, those skilled in the art without departing from the scope and spirit of the disclosure. For example, it is to be understood that this disclosure contemplates that to the extent possible, one or more features of any example or aspect can be combined with one or more features of any other example or aspect. Accordingly, the foregoing description is intended to be illustrative rather than restrictive.

We claim:

1. A fluid injector system comprising:
   a controller operably associated with at least one drive member by which at least one fluid contained within at least one fluid container is injectable into a patient,
   the controller including a programming system for enabling programming of at least one diagnostic injection procedure comprising at least one diagnostic injection phase according to which the at least one fluid is to be injected into the patient so as to effect enhancement of at least one region of interest thereof over a scan duration of a diagnostic imaging procedure; and
   the programming system for further enabling programming of a test injection procedure to be performed prior to the diagnostic injection procedure, wherein the test injection procedure is implementable as:
   a variable single phase test injection in which a flow rate at which the at least one fluid is to be delivered is selectable prior to performance of the variable single phase test injection and may be varied during performance of the variable single phase test injection.

2. The fluid injector system according to claim 1, wherein the test injection procedure is further implementable as at least one of a multi-phase test injection in which the flow rate at which the at least one fluid is to be delivered is selectable for each phase of the multi-phase test injection prior to performance of the multi-phase test injection, and a fixed single phase test injection in which the flow rate at which the at least one fluid is to be delivered and the volume of the at least one fluid to be delivered are fixed.

3. The fluid injector system according to claim 1, wherein the at least one fluid to be delivered during the variable single phase test injection is saline.

4. The fluid injector system according to claim 1, wherein, for the variable single phase test injection, a volume of the at least one fluid to be delivered is selectable prior to performance of the variable single phase test injection.

5. The fluid injector system according to claim 2, wherein, for the multi-phase test injection, a volume of the at least one fluid to be delivered is selectable prior to performance of the multi-phase test injection.

6. The fluid injector system according to claim 2, wherein, for the multi-phase test injection, a volume of the at least one fluid to be delivered is different for each phase of the multi-phase test injection.

7. The fluid injector system according to claim 2, wherein, for the multi-phase test injection, the flow rate at which the at least one fluid is to be delivered is different for each phase of the multi-phase test injection.

8. The fluid injector system according to claim 1, wherein the flow rate at which the at least one fluid is to be delivered during performance of the variable single phase test injection is varied by varying a speed of the at least one drive member.

9. The fluid injector system according to claim 8, wherein the speed of the at least one drive member is varied via manual input using a control element.

10. The fluid injector system according to claim 1, wherein the programming system is further configured to enable adjusting the flow rate at which the at least one fluid is to be delivered during the at least one diagnostic injection phase based on a desired flow rate determined during performance of the variable single phase test injection.

11. The fluid injector system according to claim 2, wherein the multi-phase test injection comprises at least a first phase having a first flow rate and a second phase following the first phase, the second phase having a second flow rate.

12. The fluid injector system according to claim 11, wherein the second flow rate is different from the first flow rate.

13. A computer program product for enabling programming of a test injection procedure to be performed using a fluid injector system prior to a diagnostic injection procedure, the computer program product comprising at least one non-transitory computer-readable medium comprising one or more instructions that, when executed by at least one processor, cause the at least one processor to:
   enable a user, via the fluid injector system, to select the test injection procedure to be performed as a variable single phase test injection such that upon selecting the variable single phase test injection, a flow rate at which at least one fluid is to be delivered during the variable single phase test injection is selectable prior to performance of the variable single phase test injection and may be varied during performance of the variable single phase test injection.

14. The computer program product according to claim 13, wherein the one or more instructions, when executed by at least one processor, further cause the at least one processor to enable the user, via the fluid injector system, to select a multi-phase test injection such that, upon selecting the multi-phase test injection, a flow rate at which at least one fluid is to be delivered during the multi-phase test injection is selectable for each phase of the multi-phase test injection prior to performance of the multi-phase test injection, or select a fixed single phase test injection such that, upon selecting the fixed single phase test injection, a flow rate at which at least one fluid is to be delivered during the fixed single phase test injection and a volume of the at least one fluid to be delivered during the fixed single phase test injection are fixed.

15. The computer program product according to claim 13, wherein the at least one fluid to be delivered during at least one of the variable single phase test injection and the multi-phase test injection is saline.

16. The computer program product according to claim 13, wherein, for the variable single phase test injection, a volume of the at least one fluid to be delivered is selectable prior to performance of the variable single phase test injection.

17. The computer program product according to claim 14, wherein, for the multi-phase test injection, a volume of the at least one fluid to be delivered is selectable prior to performance of the multi-phase test injection.

18. The computer program product according to claim 14, wherein, for the multi-phase test injection, a volume of the at least one fluid to be delivered is different for each phase of the multi-phase test injection.

19. The computer program product according to claim 14, wherein, for the multi-phase test injection, the flow rate at which the at least one fluid is to be delivered is different for each phase of the multi-phase test injection.

20. The computer program product according to claim 13, wherein the flow rate at which the at least one fluid is to be delivered during performance of the variable single phase test injection is varied by varying a speed of at least one drive member by which the at least one fluid contained within at least one fluid container is injectable into a patient.

21. The computer program product according to claim 20, wherein the speed of the at least one drive member is varied via manual input using a control element.

22. The computer program product according to claim 13, wherein the one or more instructions, when executed by at least one processor, are further configured to enable adjusting the flow rate at which the at least one fluid is to be delivered during the at least one diagnostic injection phase based on a desired flow rate determined during performance of the variable single phase test injection.

23. The computer program product according to claim 14, wherein the multi-phase test injection comprises at least a first phase having a first flow rate and a second phase following the first phase, the second phase having a second flow rate.

24. The computer program product according to claim 23, wherein the second flow rate is different from the first flow rate.

25. A computer-implemented method for performing a test injection procedure using a fluid injector system having at least one drive member by which at least one fluid contained within at least one fluid container is injectable into a patient, the method comprising:
   driving the at least one drive member, using at least one processor, at a first drive rate to deliver the at least one fluid at a first flow rate; and
   varying the first drive rate to a second drive rate different from the first drive rate to vary the flow rate at which the at least one fluid is delivered from the first flow rate to a second flow rate different from the first flow rate,
   wherein varying the first drive rate to the second drive rate comprises
   receiving user input during a variable single phase test injection, via a control element operatively connected to the at least one processor.

* * * * *

UNITED STATES PATENT AND TRADEMARK OFFICE
CERTIFICATE OF CORRECTION

PATENT NO. : 12,002,560 B2
APPLICATION NO. : 17/043883
DATED : June 4, 2024
INVENTOR(S) : Kemper et al.

Page 1 of 1

It is certified that error appears in the above-identified patent and that said Letters Patent is hereby corrected as shown below:

In the Specification

In Column 1, Line 41, delete "(MM)," and insert -- (MRI), -- therefor.

In Column 8, Line 9, delete "MIEDRAD®" and insert -- MEDRAD® -- therefor.

In Column 8, Line 10, delete "MIEDRAD®" and insert -- MEDRAD® -- therefor.

In Column 8, Line 61, delete "operates" and insert -- operate -- therefor.

In Column 13, Line 15, delete "(NV)," and insert -- (PIV), -- therefor.

In Column 15, Line 5, delete "increase" and insert -- to increase -- therefor.

In Column 15, Line 52, delete "step" and insert -- steps -- therefor.

In Column 16, Line 26, delete "increase" and insert -- to increase -- therefor.

In Column 17, Line 44, delete "step" and insert -- steps -- therefor.

Signed and Sealed this
Twenty-fourth Day of September, 2024

Katherine Kelly Vidal
*Director of the United States Patent and Trademark Office*